US00PP21387P2

(12) United States Plant Patent
Bernuetz

(10) Patent No.: US PP21,387 P2
(45) Date of Patent: Oct. 12, 2010

(54) ***ARGYRANTHEMUM* PLANT NAMED 'BONMADCIVY'**

(50) Latin Name: *Argyranthemum×hybrida*
Varietal Denomination: Bonmadcivy

(75) Inventor: Andrew Bernuetz, Silverdale (AU)

(73) Assignee: Bonza Botanicals Pty., Ltd., Yellow Rock NSW (AU)

( * ) Notice: Subject to any disclaimer, the term of this patent is extended or adjusted under 35 U.S.C. 154(b) by 0 days.

(21) Appl. No.: 12/586,348

(22) Filed: Sep. 21, 2009

(51) Int. Cl.
*A01H 5/00* (2006.01)

(52) U.S. Cl. ..... Plt./406

(58) Field of Classification Search ..... Plt./406
See application file for complete search history.

*Primary Examiner*—Annette H Para
(74) *Attorney, Agent, or Firm*—Audrey Charles

(57) ABSTRACT

A new and distinct cultivar of *Argyranthemum* plant named 'Bonmadcivy', characterized by its semi-double anemone-type ivory-colored flowers, medium green-colored foliage, and moderately vigorous, compact-mounded growth habit, is disclosed.

1 Drawing Sheet

Latin name of genus and species of plant claimed: *Argyranthemum×hybrida.*

Variety denomination: 'Bonmadcivy'.

BACKGROUND OF THE INVENTION

The present invention relates to a new and distinct cultivar of *Argyranthemum* plant botanically known as *Argyranthemum×hybrida* and hereinafter referred to by the cultivar name 'Bonmadcivy'.

The new cultivar originated in a controlled breeding program in Yellow Rock, New South Wales, Australia during June 2004. The objective of the breeding program was the development of *Argyranthemum* cultivars that are freely flowering with unique flower coloration and a freely branching, compact-upright growth habit.

The new *Argyranthemum* cultivar is the result of cross-pollination. The female (seed) parent of the new cultivar is the proprietary *Argyranthemum×hybrida* breeding selection designated 04-68, not patented, characterized by its single-type white-colored flowers, medium green-colored foliage, and moderately vigorous, compact-upright growth habit. The male (pollen) parent of the new cultivar is Madeira Crested Yellow 'Bonmadcrel' U.S. Plant Pat. No. 18,650, characterized by its semi-double type yellow-colored flowers, medium green-colored foliage, and moderately vigorous, compact, upright-mounded growth habit. The new cultivar was discovered and selected as a single flowering plant within the progeny of the above stated cross-pollination during April 2005 in a controlled environment at Yellow Rock, New South Wales, Australia.

Asexual reproduction of the new cultivar by terminal stem cuttings since April 2005 at Yellow Rock, New South Wales, Australia and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Bonmadcivy' as a new and distinct cultivar of *Argyranthemum* plant:

1. Semi-double anemone-type ivory-colored flowers;
2. Medium green-colored foliage; and
3. Moderately vigorous, compact-mounded growth habit.

Plants of the new cultivar differ from plants of the female parent primarily in flower type and color. Plants of the new cultivar differ from plants of the male parent primarily in flower color.

Of the many commercially available *Argyranthemum* cultivars, the most similar in comparison to the new cultivar is the male parent, Madeira Crested Pearl 'Bonmadcrepe', U.S. Plant Pat. No. 18,664. However, in comparison, plants of the new cultivar differ from plants of 'Bonmadcrepe' in at least the following characteristics:

1. Plants of the new cultivar have a larger disc diameter than plants of 'Bonmadcrepe';
2. Plants of the new cultivar have shorter ray florets than plants of 'Bonmadcrepe'; and
3. Plants of the new cultivar have a disc floret color different from plants of 'Bonmadcrepe'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Bonmadcivy'. The plants were grown in 4.5 inch pots for 8 weeks in a greenhouse at West Chicago, Ill.

DETAILED BOTANICAL DESCRIPTION

Figure 1:
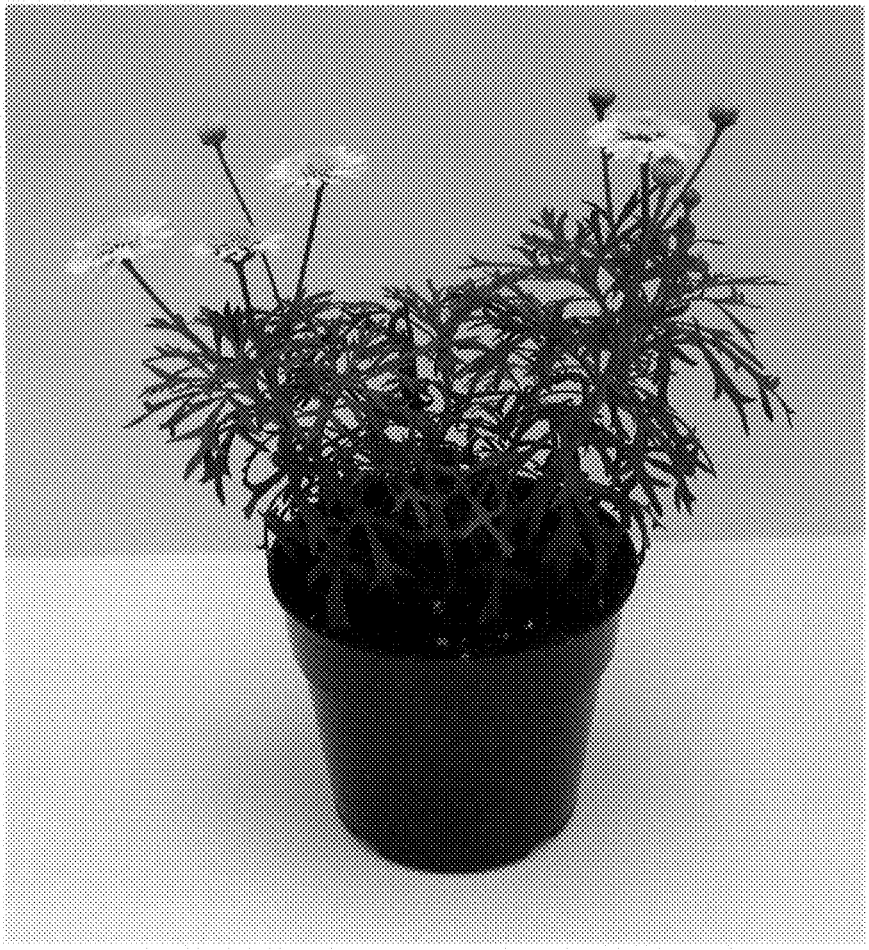
FIG. 1 illustrates a side view of the overall growth and flowering habit of 'Bonmadcivy'.
Figure 2:
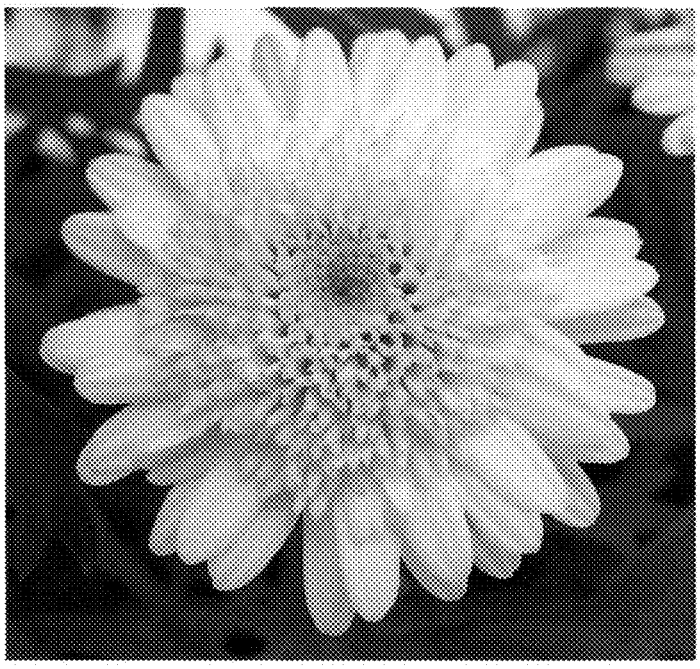
FIG. 2 illustrates a close-up view of an individual inflorescence of 'Bonmadcivy'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in September 2009 under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Argyranthemum×hybrida* cultivar Bonmadcivy.

Parentage:

*Female parent.*—Proprietary *Argyranthemum×hybrida* breeding selection designated 04-68, not patented.

*Male parent*—Madeira Crested Yellow 'Bonmadcrel' U.S. Plant Pat. No. 18,650.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 9 weeks from a rooted cutting to finish in a 10 cm pot.

*Growth habit and general appearance.*—Moderately vigorous, compact-mounded.

*Size.*—Height from soil level to top of plant plane: Approximately 18.3 cm. Width: Approximately 18.8 cm.

*Branching habit.*—Freely branching. Quantity of lateral branches per plant: Approximately 5.

*Branch.*—Strength: Strong. Length of main stem to base of peduncle: Approximately 10.8 cm. Diameter at central internode: Approximately 3.0 mm. Length of central internode: Approximately 5.3 mm. Texture: Glabrous. Color of young stem: Glaucous, 144B. Color of mature stem: Glaucous, 144B with woody base of 199B.

Foliage description:

*General description.*—Quantity of leaves per main stem: Approximately 13. Fragrance: Slight. Form: Simple. Arrangement: Alternate.

*Leaves.*—Aspect: Acute angle to stem; leaf blade obtuse angle to stem with age. Shape: Obovate. Margin: Parted. Apex: Acute, cuspidate. Base: Attenuate, decurrent. Venation pattern: Pinnate. Length of mature leaf: Approximately 6.5 cm. Width of mature leaf: Approximately 5.5 cm. Texture of upper surface: Glabrous with sparsely pubescent midvein. Texture of lower surface: Glabrous with sparsely pubescent midvein. Color of upper surface of young and mature foliage: Glaucous, 137A with venation of 146D to indistinguishable. Color of lower surface of young and mature foliage: 137C with venation of 146D to indistinguishable.

Flowering description:

*Flowering habit.*—'Bonmadcivy' is freely flowering under outdoor growing conditions with substantially continuous blooming from spring through autumn and year-round in greenhouse environment.

*Lastingness of individual inflorescence on the plant.*—Approximately 13 to 14 days.

Inflorescence description:

*General description.*—Type: Solitary, composite. Persistent. Shape: Round. Aspect: Facing upward and outward. Arrangement: Terminal, positioned above the foliage. Disc and ray florets develop acropetally on a capitulum. Quantity per plant: Approximately 5. Diameter: Approximately 3.4 cm. Fragrance: Slight.

*Peduncle.*—Strength: Strong, pliable. Aspect: Erect. Length: Approximately 5.6 cm. Diameter: Approximately 2.0 mm. Texture: Sparsely pubescent. Color: Glaucous, 144A.

*Bud.*—Rate of opening: Generally takes 6 to 7 days for bud to progress from first color to fully open flower. Quantity per plant: Approximately 8.

*Bud just before opening.*—Shape: Ovoid. Diameter: Approximately 7.0 mm. Color: 155C.

*Ray florets.*—Quantity per inflorescence: Approximately 41. Arrangement: Imbricate in two whorls. Aspect: Slightly convex, tuning downward with age. Shape: Ligulate. Margin: Entire. Apex: Emarginate with 3 tips to rounded. Base: Attenuate, fused to form a tube. Length: Approximately 1.4 cm. Width: Approximately 5.0 mm. Texture of upper surface: Glabrous. Texture of lower surface: Glabrous, ribbed. Color of upper surface when first and fully open: 155A. Color of lower surface when first and fully open: Purer white than 155D.

*Disc florets.*—Quantity per inflorescence: Approximately 162. Arrangement: Massed in center of inflorescence. Shape: Tubular with 5 lobes. Margin: Entire. Apex: Acute. Base: Truncate. Length: Approximately 7.0 mm. Diameter at apex: Approximately 3.0 mm. Diameter at base: Approximately 1.0 mm. Texture: Glabrous with glandular pubescence on lower half. Gland color: Colorless. Color when fully open: 145D with 155A at lobes.

*Disc.*—Diameter: Approximately 2.1 cm. Depth: Approximately 7.0 mm.

*Receptacle.*—Shape: Cone. Height: Approximately 3.0 mm. Diameter at base: Approximately 4.5 mm. Color: 145B.

*Phyllaries.*—Quantity per inflorescence Approximately 23. Arrangement: Imbricate, in several whorls. Shape: Lanceolate. Margin: Entire. Apex: Acute. Base: Truncate. Length: Approximately 5.0 mm. Width: Approximately 2.5 mm. Texture of upper and lower surfaces: Glabrous, papery along edges. Color of upper surface: 143A in center with transparent margins of N199B. Color of lower surface: Closest to 143C in center with transparent margins of N199B.

*Reproductive organs.*—Androecium: Present on disc florets only. Stamen quantity: 5 per floret. Stamen length: Approximately 3.0 mm. Anther shape: Linear. Anther length: Approximately 1.0 mm. Anther color: 21B. Pollen amount: Abundant. Pollen color: 17B. Gynoecium: Present on ray and disc florets. Pistil quantity: 1 per floret. Pistil length: Approximately 6.0 mm. Stigma shape: Two-parted. Stigma length: Less than 1 mm. Stigma color: 1D. Style length: Approxi mately 4.0 mm. Style color: 145D, transparent. Ovary length: Approximately 2.0 mm. Ovary color: 145D.

Seed and fruit production: Neither seed nor fruit production has been observed.

Disease and pest resistance: Resistance to pathogens and pests common to *Argyranthemum* has not been observed.

What is claimed:

1. A new and distinct cultivar of *Argyranthemum* plant named 'Bonmadcivy', substantially as herein shown and described.

* * * * *